United States Patent [19]

Valen

[11] Patent Number: 4,459,111
[45] Date of Patent: Jul. 10, 1984

[54] CROWN AND BRIDGE PREFABRICATED SYSTEM AND IMPLANT

[76] Inventor: Maurice Valen, 198-45 Foothill Ave., Holliswood, Queens, N.Y. 11423

[21] Appl. No.: 274,773

[22] Filed: Jun. 18, 1981

[51] Int. Cl.³ ............................................. A61C 8/00
[52] U.S. Cl. .................................................... 433/176
[58] Field of Search ................. 433/176, 204, 205, 210

[56] References Cited

U.S. PATENT DOCUMENTS

| | | | |
|---|---|---|---|
| 3,672,058 | 6/1972 | Nikoghossian | 433/176 |
| 3,881,251 | 5/1976 | Valen | 433/176 |
| 3,977,081 | 8/1976 | Zambelli et al. | 433/176 |
| 4,024,638 | 5/1977 | Linkow et al. | 433/176 |
| 4,024,639 | 5/1977 | Weiss | 433/173 |

FOREIGN PATENT DOCUMENTS

| | | | |
|---|---|---|---|
| 2237598 | 2/1974 | Fed. Rep. of Germany | 433/176 |
| 296827 | 2/1954 | Switzerland | 433/172 |

*Primary Examiner*—Robert Peshock
*Attorney, Agent, or Firm*—Robert S. Salzman

[57] ABSTRACT

This invention relates to a prosthetic dental tooth implant for anchoring a tooth to the jaw bone of an individual. The device is a blade like section having a number of circular holes having a slot-like aperture in a bottom portion of the blade to provide flexure of the blade and outwardly bendable prong extending from a top portion of each hole for anchoring engagement against an inner surface of the cortical plates adjacent the aveolar tissue of the jaw bone.

9 Claims, 8 Drawing Figures

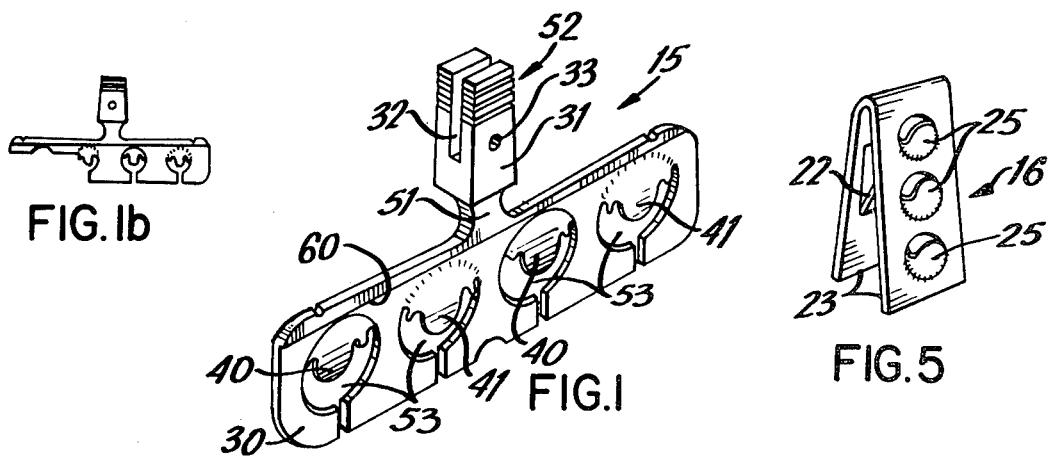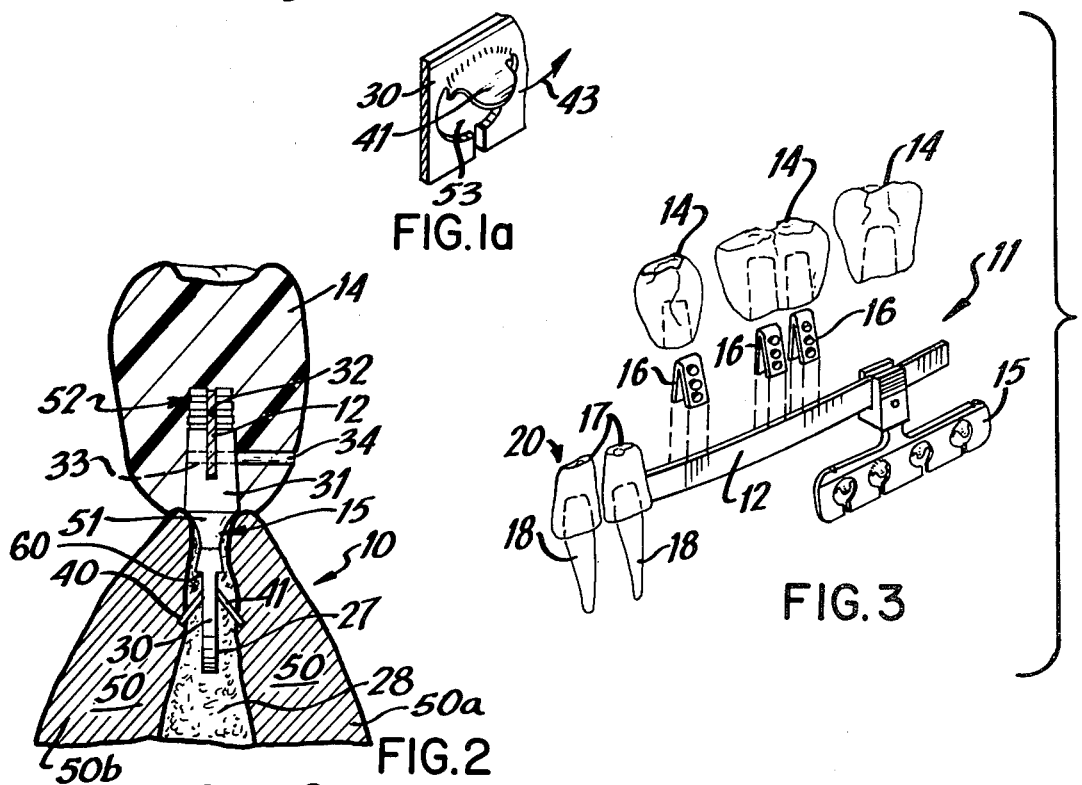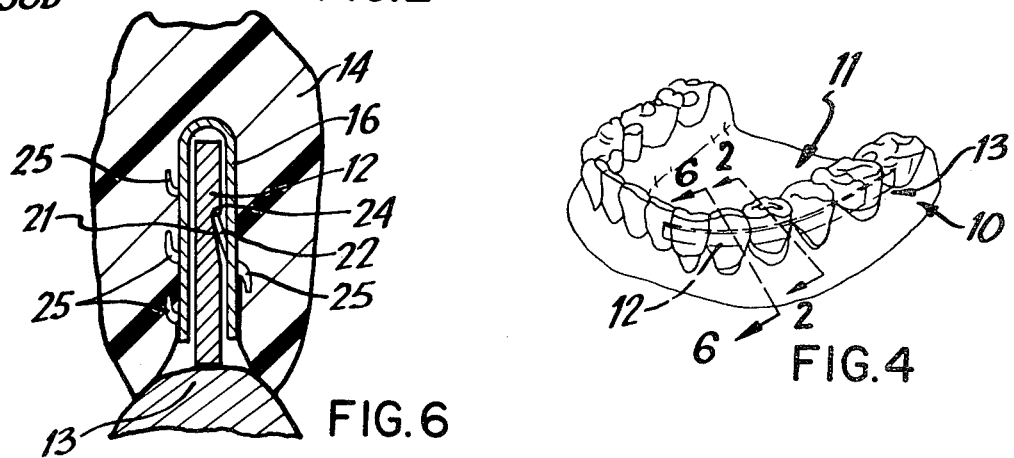

CROWN AND BRIDGE PREFABRICATED SYSTEM AND IMPLANT

RELATED APPLICATIONS

This application is related to U.S. Pat. Nos. 3,866,321; issued: Feb. 18, 1975, and 3,881,251; issued: May 6, 1975. The present invention is an improvement over the above-mentioned patents. Insofar as the aforementioned patents may have certain similarities to the present invention, the teachings therein are meant to be incorporated herein by way of reference.

FIELD OF THE INVENTION

This invention relates to prosthetic dental devices, and more particularly to an artificial tooth assembly and implant of improved design and functionality.

BACKGROUND OF THE INVENTION

Heretofore, bridge-like structures were built with the intention of anchoring these systems to the alveolar bone of the jaw by means of implants. Such bridge-like structures are shown in the aforementioned related patents and also in the U.S. Pat. No. 4,050,157 to Fagan, Jr. et al., issued: Sept. 27, 1977.

In the latter related patents, the implant has flexible cups which are designed to engage with the soft alveolar bone tissue in order to sustain the lateral and occlusal loading forces of mastication.

In the patent to Fagan, Jr. et al., a stabilizer is used to engage the soft alveolar bone of the jaw in order to secure and provide additional anchoring stability against shifting masticatory loads.

While both these systems were useful for their time, they were not able to sustain severe loading forces in a downward direction. This was so, because the soft alveolar bone tissue would yield under extreme compressive forces, i.e. pressures of 150 pounds per square inch or more. In some unfortunate situations, these extreme downward forces would cause necrosis of the alveolar tissue, requiring removal of the implant and its artificial tooth structure.

The present invention seeks to build upon these old teachings and preserve the structuralability of these systems to sustain lateral and occlusal loads.

The present invention seeks to improve upon these teachings by improving the ability of the implant to sustain extreme downwardly directed forces.

The inventive system sustains the molar masticatory forces by anchoring the implant within the soft alveolar bone as before, but supports the implant blade upon the hard cortical plates of the jaw. The implant invention features bendable prongs that engage with, and rest upon, lingual and buccal cortical plates. The cortical plates being a hard portion of the jaw bone, are better adapted to sustain the downwardly directed forces applied to the implant.

The artificial tooth assembly of the invention also features parts which snap together for ease of assembly and disassembly.

BRIEF SUMMARY OF THE INVENTION

The invention pertains to an artificial tooth assembly for placement in a mouth of an individual, in that portion thereof requiring replacement of at least one missing natural tooth. The artificial tooth assembly is an operatively viable and simulative replacement for the natural missing teeth. The assembly comprises a bar extending across and anchored within the replacement portion of the mouth. The bar has a notch disposed on a side thereof for receiving at least one clip. The clip is used to anchor a tooth or tooth-like prosthesis to the flexible bar. The clip has a number of flexible tines. At least one tine of the clip engages with the groove in the bar. The other tines engage with the tooth or tooth-like prosthesis.

A blade-like implant is secured to the bar and disposed within the jaw bone. The implant anchors the bar and/or a tooth to the jaw bone. The implant comprises a blade-like section for implantation within the soft aveolar jaw bone tissue. The blade-like section has a number of outwardly bendable prongs for anchoring engagement against the lingual and buccal cortical plates of the jaw bone. The prongs are designed to support the blade-like section experiencing downwardly directed masticatory forces.

At least one stem section extends from the blade-like section and is designed to receive the tooth or tooth-like prosthesis.

The prongs in the blade-like section are alternately outwardly bendable in lingual and buccal directions.

It is an object of this invention to provide an improved crown and bridge system including an artificial tooth assembly anchored by an improved implant;

It is another object of the invention to provide an implant which can sustain downwardly directed masticatory forces;

It is another object of this invention to provide an artificial tooth assembly which is easily assembled and disassembled.

These and other objects of the invention will be better understood and will become more apparent with reference to the following detailed description considered in conjunction with the accompanying drawings.

BRIEF DESCRIPTION OF THE DRAWINGS

FIG. 1 is a perspective view of the implant of the invention;

FIG. 1a is a partial perspective view of the implant of FIG. 1, illustrative of a prong portion with the prong bent outwardly so as to engage a cortical plate of the jaw bone;

FIG. 1b is a side view of a modified implant;

FIG. 2 is a cross-sectional view of an implant and tooth assembly depicting the functionality of the implant supported upon the lingual and buccal cortical plates of the jaw bone as taken along lines 2—2 of FIG. 4;

FIG. 3 is a perspective exploded view of an artificial tooth assembly secured to the implant shown in FIG. 1;

FIG. 4 is a perspective view of the artificial tooth system of this invention as illustrated in situ within the mouth of an individual;

FIG. 5 is a perspective view of a clip used in the artificial tooth assembly of FIG. 3; and FIG. 6 is a cross-sectional view of the artificial tooth assembly as taken along lines 6—6 of FIG. 4.

DETAILED DESCRIPTION OF THE INVENTION

Generally speaking, the invention features an easily assembled artificial tooth assembly which is anchored to the jaw bone by an implant which is designed to withstand downwardly directed masticatory forces.

Referring to FIG. 4, a lower jaw 10 is shown supporting an artificial tooth assembly 11 in situ. The artificial tooth section 11 is shown in an exploded view in FIG. 3. The artificial tooth assembly 11 comprises a bar 12 that is adjacent the top of the gum 13 of the jaw 10.

An implant 15 anchors bar 12 to the jaw bone 10, as will be described in more detail hereinafter with reference to FIG. 2.

The artificial tooth assembly is generally comprised of artificial teeth 14 which are attached to bar 12 by means of clips 16. Some larger teeth, such as molars may be secured to bar 12 by more than one clip 12 as shown by the middle tooth 14 in FIG. 3. The artificial teeth fill the space vacated by the missing natural teeth. Part of the tooth assembly 11 (FIG. 3) may be comprised of prepared teeth 20, which are comprised of posts 18 having caps 17 cemented thereon. The posts 18 can be fabricated by filing down a natural tooth. Also, endodontic posts may be utilized. The endodontic posts can be cemented into a natural tooth root, or attached to an implant 15. The bar 12 may be terminally anchored to a natural or prepared tooth.

In the aforementioned U.S. Pat. Nos. 3,881,251, and 3,866,321, it was taught that the artificial tooth assembly 11 should be easily assembled and disassembled to further the concept of mass production fabrication. Mass production techniques help to lower the cost of crown and bridge assemblies, which are currently specifically fashioned to each individual.

The present invention seeks to improve upon these teachings by suggesting further improvements in construction. Referring to FIGS. 5 and 6, the present invention illustrates how the artificial teeth 14 may be secured to the top of gum 13 by means of an improved bar 12 and clip 16. The improved bar 12 and clip 16 of this invention feature a new snap-in locking system, which allows for easier assembly and disassembly of the artificial bridge section 11. The bar 12 is constructed with a groove 21, which receives a tine 22 of clip 16. The tine 22 is bent inwardly, so that when the clip 16 is forced downwardly over the bar 12, the tine 22 will snap into groove 21 in bar 12. Groove 21 runs the length of bar 12, and is generally on only one side thereof, although it is contemplated that a groove 21 may run along both sides of the bar 12 in order to engage tines 22 on both inner surfaces of clip 16 (not shown).

The clip 16 is constructed with a general U-shaped appearance to fit tightly about bar 12, as shown in the engaged position in FIG. 6.

FIG. 5 depicts the clip 16 with legs 23 spread slightly apart. When an artificial tooth 14 having an internal hollow portion is placed over clip 16, the legs 23 are forced together, causing tine 22 to engage more securely with the upper lip 24 of groove 21.

Clip 16 has other tines 25, which secure the artificial tooth 14 to clip 16. These tines 25 can be both upwardly and downwardly disposed, so that the artificial tooth will not move in either direction when anchored to bar 12 by clip 16. Misial distal movement is prevented by neighboring teeth disposed on each side of the tooth 14.

Each tooth 14 can be quickly and easily snapped into place along the bar 12, until an entire bridge section 11 is completed as shown in FIG. 4.

The bridge assembly 11 is anchored to the jaw bone 10 by means of the implant 15, as aforementioned. The implant 15 is designed to secure the bridge section 11 to the jaw bone 10 in a more positive manner than heretofore known or suggested by prior implants.

Generally speaking, the implant 15 is placed in a prepared groove 27 within the soft alveolar bone 28 of the jaw bone 10, as shown in FIG. 2. Unlike prior implants, the inventive implant 15 is not supported by the alveolar tissue. This tissue is too soft to support extreme downward forces, as can be generated in the molar area of the jaw 10. If the thin blade section 30 of implant 15 rests upon the aveolar bone 28, extreme downward loading can cause necrosis of the aveolar tissue. This then would necessitate removal of the bridge assembly 11.

Referring to FIGS. 1, 1a and 2, implant 15 is shown having a thin blade section 30, and a truncated stem section 31. The stem section 31 has a slot 32 for receiving bar 12. A hole 33 in stem 31 is adapted to receive a pin 34 to secure both the artificial tooth 14 and bar 12 to implant 15, which in turn anchors the bridge assembly (teeth and bar) to jaw bone 10.

Blade-like section 30 has a number of bendable prongs 40 and 41, respectively. These prongs 40, 41 are respectively alternately disposed on opposite sides of blade section 30. The prongs 40, 41 are each bent outwardly from a top portion of each hole 53 as typically shown by arrow 43 in the cutaway view of section 30, in FIG. 1a. When the implant 15 is inserted in groove 27 of the aveolar bone 28, prongs 40 and 41 engage, and rest upon, the hard cortical plates 50, as illustrated in FIG. 2. Prongs 41 engage the lingual plate 50a, while prongs 40 engage with the buccal plate 50b.

The neck 51 of implant 15 is designed to rest at the top of cortical plates 50 to provide added support.

The grooves 52 in the truncated stem 31 are designed to aid in further cementing of the tooth 14 to stem 31.

Implant 15 may be modified as shown in FIG. 1b, in order to fit in other areas of the jaw bone 10 (generally in a maxilla mouth area).

The implant is generally made of titanium, which is compatible with the mouth tissue. Circular holes 53 disposed adjacent each prong 40, 41 allow the aveolar tissue to grow through the blade section 30, thus adding structural and functional integrity to the implant 15. Holes 30 each have slot-like apertures in a bottom portion thereof to provide for flexure of the blade section 30. The misial distal ridge 60 provides additional distribution of the occlusal load.

More than one implant 15 may be used if needed to secure a longer bridge section 11.

The teeth may be molded from plastic materials.

The bar 12 may be made of gold or stainless steel so as to be bent to the proper shape of the mouth portion receiving assembly 11, as depicted in FIGS. 3 and 4.

Clips 12 may be comprised of stainless steel.

Having thus described the invention, what is desired to be protected by Letters Patent is presented by the following appended claims.

What is claimed is:

1. A tooth implant for anchoring a tooth or tooth-like prosthesis to the jaw bone of an individual, comprising:
a blade-like section for implantation within soft aveolar jaw bone tissue, said blade-like section having a number of substantially circular holes having a slot-like aperture in a bottom portion of said blade to provide for flexure of the blade and outwardly bendable prongs extending from a top portion of each of said holes for anchoring engagement against an inner surface of the cortical plates adjacent said aveolar tissue of said jaw bone, said prongs designed to support said blade-like section experiencing downwardly directed masticatory forces, and at least one stem section extending from said blade-like section and designed to receive a tooth or tooth-like prosthesis.

2. The tooth implant of claim 1, wherein said blade-like section has at least two prongs, one of said two prongs for engagement against a lingual cortical plate and the other of said two prongs for engagement against a buccal cortical plate.

3. The tooth implant of claim 1, wherein said stem section has a slot in an end portion thereof, for receiving a bar member of an artificial tooth assembly.

4. The tooth implant of claim 1, wherein said stem section has an aperture therein for receiving a pin fastener for securing said tooth or tooth-like prosthesis.

5. The tooth implant of claim 1, wherein said stem section has a truncated shape.

6. The tooth implant of claim 1, wherein said blade-like section has an aperture adjacent each prong.

7. The tooth implant of claim 1, wherein said blade-like section can be shaped to fit different areas of said jaw bone.

8. The tooth implant of claim 1, wherein said prongs are alternately outwardly bendable from said blade-like section in lingual and buccal directions.

9. The tooth implant of claim 1, wherein said stem section has grooves in a top portion thereof, for securing said tooth or tooth-like prosthesis.

* * * * *